United States Patent [19]
Maeda et al.

[11] Patent Number: 5,824,829
[45] Date of Patent: Oct. 20, 1998

[54] HYDROCARBON VISCOSITY INHIBITOR AND INHIBITING METHOD

[75] Inventors: Noriaki Maeda, Kurashiki; Toru Taguchi, Yokkaichi; Seiji Tanizaki, Mie prefecture; Nobumitsu Kumazawa; Yutaka Takeuchi, both of Yokkaichi, all of Japan

[73] Assignee: Baker Hughes Incorporated, Houston, Tex.

[21] Appl. No.: 861,922

[22] Filed: May 22, 1997

Related U.S. Application Data

[63] Continuation-in-part of Ser. No. 355,607, Dec. 14, 1994, abandoned.

[30] Foreign Application Priority Data

Dec. 16, 1993 [JP] Japan ................................ 5-316697

[51] Int. Cl.$^6$ ................. C07C 7/20; C09K 3/00
[52] U.S. Cl. .................. 585/3; 585/4; 585/435; 252/574; 252/395
[58] Field of Search .................. 585/3, 4, 435; 252/574, 395

[56] References Cited

U.S. PATENT DOCUMENTS

| | | | |
|---|---|---|---|
| 3,617,478 | 11/1971 | King, Jr. et al. | 208/48 AA |
| 4,425,223 | 1/1984 | Miller, I | 208/48 AA |
| 4,440,625 | 4/1984 | Go et al. | 208/48 AA |
| 4,654,450 | 3/1987 | Miller, II | 585/5 |
| 4,929,778 | 5/1990 | Roling | 585/3 |

OTHER PUBLICATIONS

*Chemical Abstracts* 97:8749z (1982).
*Chemical Abstracts* 98:146371s (1983).
*Chemical Abstracts* 101:75484y (1984).

*Primary Examiner*—Elizabeth D. Wood
*Attorney, Agent, or Firm*—Rosenblatt & Redano P.C

[57] ABSTRACT

An inhibitor to suppress or inhibit the viscosity increase of a hydrocarbon, e.g. in a bottom section of an oil quench tower, featuring the use of a sulfonic acid and/or its salt as an effective inhibitor composition, which may optionally contain a polymerization inhibitor including one or more inhibitors selected from the group of aromatic amines, phenols and dialkyl hydroxyl amines. Furthermore, the method to inhibit the increasing viscosity of hydrocarbon, e.g. in a bottom section of a tower, may be accomplished by adding the hydrocarbon viscosity inhibitor to the feed oil, reflux oil or directly to the tower bottom oil in the tower. Such an oil quench tower is used for an olefin production process in which the hydrocarbon may include naphtha, light oil, natural gas, liquefied natural gas, etc. in the raw material.

6 Claims, No Drawings

HYDROCARBON VISCOSITY INHIBITOR AND INHIBITING METHOD

This is a continuation-in-part of copending application Ser. No. 08/335,607 filed on Dec. 14, 1994, and now abandoned.

FIELD OF THE INVENTION

The present invention relates to hydrocarbon viscosity inhibitors or reducers and methods of inhibiting or reducing the viscosity of hydrocarbons, and more particularly relates to hydrocarbon viscosity inhibitors which also increase hydrocarbon product yield, improve the thermal effect of and stabilize operation by inhibiting or reducing the viscosity of a hydrocarbon.

BACKGROUND OF THE INVENTION

In the petrochemical industry, various types of olefins are usually produced by thermally decomposing naphtha. Naphtha together with diluting stream is thermally decomposed at about 800° to about 850° C. in a thermal decomposition furnace, abruptly cooled down to about 350° to about 400° C. at the outlet of the decomposition furnace and sent to an oil quench tower (also called a gasoline fractionator or gasoline splitter) in which the naphtha is divided into a light component with 9 or less carbon atoms, and a heavy component with more than 9 carbon atoms. The feed oil in the quench tower contains the aromatic unsaturated compounds of the styrene, methyl styrene, divinylbenzene, indene, etc., which can be undesirably polymerized by the heat throughout the oil quench tower thus increasing the viscosity of oil in the bottom section of the tower and thus cause contamination by polymerized materials in the tower. In the past, the contamination of the tower has been prevented by adding a polymerization inhibitor, but such a method showed only a limited preventative effect, and did not inhibit or reduce the viscosity of the oil from increasing in the tower. Therefore, the method commonly used for inhibiting the increase of viscosity of oil in the bottom section of the tower was to lower the temperature of tower bottoms.

SUMMARY OF THE INVENTION

Accordingly, it is an object of the present invention to provide a chemical agent and a method which can inhibit the viscosity of hydrocarbon from increasing, e.g. in the bottom section of an oil quench tower in an olefins production process.

It is another object of the present invention to provide a hydrocarbon viscosity inhibitor or reducer which can be readily acquired or made.

In carrying out these and other objects of the invention, there is provided, in one form, a hydrocarbon viscosity inhibitor composition comprising a sulfonic acid or salt thereof of the formula: $R'—SO_3(X)_n$. In this formula, R' is selected from the group consisting of a straight or branched alkyl group of 4–32 carbon atoms; an alkyl-substituted benzene nucleus and an alkyl-substituted naphthalene nucleus, where the alkyl group in either is a straight or branched alkyl group of 4–32 carbon atoms; X is selected from the group consisting of hydrogen, alkali metal, and alkali earth metal, primary amine salt, secondary amine salt, tertiary amine salt; where any of the amine salts may be substituted with a straight or branched alkyl group of 1–22 carbon atoms, and further where the straight or branched alkyl group of 1–22 carbon atoms may contain a hydroxy or an alkoxy group, and n is selected from the group consisting of 1 or ½.

DETAILED DESCRIPTION OF THE INVENTION

It was assumed that the increase in viscosity of a hydrocarbon in, for example, the bottom of equipment such as an oil quench tower is caused by the thermal polymerization of aromatic unsaturated compounds of styrene, methyl styrene, divinylbenzene, indene, etc. contained in the feed oil. Based on this assumption, a very strenuous and diligent study was made regarding the inhibition of polymerization and increase in viscosity, which resulted in the discovery of a compound which can inhibit the viscosity of a hydrocarbon from increasing in the tower bottom.

The invention of inhibiting or suppresses the rising viscosity of hydrocarbon in the bottom section of an oil quench tower, e.g., features the use of one or more components of sulfonic acid or its salt of the formula (I):

$$R'—SO_3(X)_n \qquad (I)$$

where R' is selected from the group consisting of
  a straight or branched alkyl group of 4–32 carbon atoms;
  an alkyl-substituted benzene nucleus, where the alkyl group is a straight or branched alkyl group of 4–32 carbon atoms; and
  an alkyl-substituted naphthalene nucleus, where the alkyl group is a straight or branched alkyl group of 4–32 carbon atoms;
  X is selected from the group consisting of hydrogen, alkali metal, and alkali earth metal, primary amine salt, secondary amine salt, tertiary amine salt; where any of the amine salts may be substituted with a straight or branched alkyl group of 1–22 carbon atoms, and further where the straight or branched alkyl group of 1–22 carbon atoms may contain a hydroxy or an alkoxy group; and
  n is selected from the group consisting of 1 or ½.

It will be appreciated that when X is hydrogen, the above formula (I) is a sulfonic acid, and when X is other than hydrogen, it is a salt form that is being referred to.

Furthermore, this is an inhibitor composition which suppresses the rising viscosity of the aforementioned hydrocarbon, a feature of which is to mix one or more polymerization inhibitors selected from the aromatic amine family of polymerization inhibitors, the phenol family of polymerization inhibitors and the dialkyl hydroxylamine family polymerization inhibitor with the $R'—SO_3(X)_n$ component. This invention is also related to a method to inhibit an increase in viscosity of a hydrocarbon, such as in the bottom section of oil quench tower, involving addition of the subject viscosity inhibitor to the tower bottom oil using the effective component of sulfonic acid or its salt of formula (I). In one embodiment, the proportion of sulfonic acid or its salt or the composition containing the same is from about 10 ppm to about 10,000 ppm based on the amount of oil in the tower bottom or other hydrocarbon.

In non-limiting, more specific examples of suitable components of this invention are the sulfonic acid or its salt shown in formula (1) where R includes, but is not limited to, nonyl, decyl, dodecyl, octadecyl, petroleum sulfonic acid residue, dodecyl benzene, tridecyl benzene, dibutyl benzene, octyl benzene, nonylbenzene, or nonyl naphthenate. In the formula (I), X can be hydrogen or alkaline metals such as lithium, sodium, potassium, etc., or alkaline earth metals such as magnesium, barium, calcium, etc. or alkyl amine salts such as propyl amine salt, diisopropyl amine salt, diisobutyl amine salt, sec-butyl amine salt, di-sec-butyl amine salt, 1,2-dimethyl propyl amine salt, hexyl amine salt, cyclohexyl amine salt, heptyl amine salt, 2-ethyl hexyl amine salt, di(2-ethylhexyl) amine salt, octyl amine salt, nonyl amine salt, decyl amine salt, undecyl amine salt, dodecyl amine salt, tetra decyl amine salt, hexadecyl amine salt, octadecyl amine salt, coco amine salt, mono-ethanol amine salt, etc. More specific examples include, but are not limited to dodecyl benzene sulfonic acid sodium, petroleum sulfonic acid sodium, dodecyl benzene sulfonic acid coco amine salt, dodecyl benzene sulfonic acid mono-ethanol amine salt, etc. Each of these sulfonic acids and their salts may be used individually alone or in combination of two or more suitable sulfonic acids or their salts, and this invention does not restrict or limit the mixed use of these acids and salts.

The optional polymerization inhibitor of this invention may be generally defined as an oxidation inhibitor which reacts based on the radical chain inhibiting reaction. The aromatic amine family of polymerization inhibitors include, but are not necessarily limited to, p-phenylenediamines such as N,N'-di-di-isopropyl-p-phenylenediamine; N,N'-di-sec-butyl-p-phenylenediamine; N,N'-diphenyl-p-phenylenediamine; N-(1-methylheptyl)-p-phenylenediamine; etc.; and secondary amines such as 4,4-dicumyl-diphenyl amine; 4,4-dioctyl diphenyl amine; p-methoxy phenylmethylamine; 4,4-dinonyl diphenylamine; diphenylamine; phenyl-α-naphthylamine; phenyl-β-naphthylamine; etc. Suitable polymerization inhibitors from the phenol family include, but are not necessarily limited to, the following various types of phenols: phenol; 2-methyl phenol; 4-methyl phenol; 2,6-dimethyl phenol; 2,4,6-trimethyl phenol; 2,6-ditertiary butyl phenol; 2,4-ditertiary butyl phenol; 2-methyl-4-tertiary butyl phenol; 2,6-diisopropyl phenol; 2,6-dimethyl-4-tertiary butyl phenol, 4-methoxyl phenol, etc. and various catechols including, but not limited to, 4-tertiarybutyl catechol, and various hydroquinones including, but not necessarily limited to, hydroquinone; 2-methyl hydroquinone; 2-tertiary butyl hydroquinone; 2,5-di-tertiary butyl hydroquinone; 2,5-di-tertiary amyl hydroquinone, etc. The dialkyl hydroxyl amine family of polymerization inhibitors includes, but is not limited to such materials as diethylhydroxylamine; dipropylhydroxylamine, etc.

In one embodiment of the invention, a dialkylhydroxylamine is explicitly absent, and in particular, diethylhydroxylamine (DEHA) is explicitly absent.

Each of these polymerization inhibitors may be used singly with the viscosity inhibitor or in combination of two or more inhibitors together with the sulfonic acids or salts thereof. This invention is not limited to any particular mixture of these inhibitors or mixture of inhibitors with the viscosity inhibitors of this invention.

The optional polymerization inhibitor of this invention may be used by mixing it with the viscosity inhibitor sulfonic acid or its salt, where the ratio of polymerization inhibitor to the sulfonic acid of formula (I) or its salt is 10 to 1 or less, by weight. The hydrocarbon viscosity inhibitor composition of this invention is added to the oil in the bottom of an oil quench tower or other hydrocarbon in a proportion of about 10 to about 10,000 ppm, preferably about 10 ppm to about 2,000 ppm, based on the amount of hydrocarbon. Normally amounts in these ranges are expected to be effective, although other proportions are also anticipated to be effective. However, in general, if the proportion is less than about 10 ppm, an effective result normally cannot be ensured, and if the proportion is more than 10,000 ppm, the effect may be sufficient, but not in a cost effective proportion to the amount added.

In the practice of the method of this invention, the hydrocarbon viscosity inhibitor composition may be added at other positions, but in the oil quench tower application, it is normally added to the tower feed oil or return oil, or directly to the oil in the bottom of an oil quench tower.

When adding the viscosity inhibitor of this invention, each effective component of the inhibitor may be added separately, or may alternatively be mixed at the specified proportions before adding. For easy addition, it is usually better to measure the amount of each effective component and dissolve it in an appropriate solvent before injecting.

Since it is assumed that the increase in the viscosity of tower bottom oil flowing out of oil quench towers after distilling is caused by the polymerization of aromatic unsaturated compounds such as ethylene, methyl ethylene, divinylbenzene, indene, etc., the viscosity increase may be inhibited by suppressing the polymerization. However, the effective viscosity inhibition has not been made with the conventional polymerization inhibitors alone. The viscosity inhibitors of this invention are believed to prevent the viscosity from increasing as the inhibitor adheres to the initially formed polymer and disperses the formed polymer, thus preventing the polymerization from further progressing and the formed polymer from branching and bridging. However, the inventors do not wish to be limited by any particular theory.

This invention is explained further and in more detail by the following examples of actual application, but is not limited to the illustrated examples alone.

TABLE I

Viscosity Inhibitors Used for Tests

| Viscosity inhibitor shorthand | Viscosity inhibitor type | Viscosity inhibitor description |
|---|---|---|
| A | Sulfonic acid | Dodecyl benzene sulfonic acid (branched type) free acid |
| B | Sulfonic acid salt | Dodecyl benzene sulfonic acid (branched type)/ tetradecyl amine salt; prepared by dissolving equimolar amounts of the sulfonic acid and the amine in xylene; kept at 60° C. for 2 hours, thus forming salt. For this testing, the xylene solution as simply added. |

TABLE I-continued

Viscosity Inhibitors Used for Tests

| Viscosity inhibitor shorthand | Viscosity inhibitor type | Viscosity inhibitor description |
|---|---|---|
| C | Sulfonic acid salt | Dodecyl benzene sulfonic acid (branched type)/cocoamine salt |
| D | Sulfonic acid salt | Dodecyl benzene sulfonic acid (branched type)/2-ethylhexyl amine salt |
| B | Sulfonic acid salt | Dodecyl benzene sulfonic acid (branched type) / dibutyl amine salt |
| F | Sulfonic acid salt | Dodecyl benzene sulfonic acid (branched type)/ethylene diamine salt |
| G | Sulfonic acid salt | Dodecyl benzene sulfonic acid (branched type) / monoethanol amine salt |
| H | Sulfonic acid salt | Dodecyl benzene sulfonic acid (straight chain type)/tetradecyl amine salt |
| I | Sulfonic acid salt | Tridecyl benzene sulfonic acid (branched type)/tetradecyl amine salt |
| J | Sulfonic acid salt | Tetradecyl benzene sulfonic acid (branched type)/n-butyl amine salt |
| K | Sulfonic acid salt | Petroleum sulfonic acid/sodium salt |
| L | Sulfonic acid salt | Petroleum sulfonic acid/sodium salt |

TABLE II

Polymerization Inhibitors Used for Tests

| Abbrev., if any | Full name | Source | Trade name, if any |
|---|---|---|---|
| TBC | 4-tert-butyl catechol | Dainippon Ink & Chemicals Inc. | DIC-TBC |
| BHT | 2,6-dimethyl-p-cresol | Kawaguchi Chemicals Inc. | Antage BHT |
| BPA | N,N'-di-sec-butyl-p-phenylenediamine | Sumitomo Chemicals Inc. | Sumlizer BPA |
| DEHA | Diethyl hydroxylamine | Toka Idenka Kogyo Inc. | DEHA |
| DPA | Diphenylamine | Seiko Chemicals Inc. | |
| | Polymethacrylate family of dispersion agents | Texaco Chemical Co. | |

TABLE III

Raw Materials Used in Polymerization Inhibitors Used for Tests

| Full name | Source | Trade name, if any |
|---|---|---|
| Dodecyl benzene sulfonic acid (branched type) | Teika | Teika Power B-120 |
| Dodecyl benzene sulfonic acid (straight chain type) | Teika | Teika Power L-120 |
| Tridecyl benzene sulfonic acid (branched type) | Teika | Teika Power B-130 |
| Petroleum sulfonic acid sodium salt | Matsumura Sekiyu | Sulforl 500 |
| Tetra decyl amine | Nihon Yushi | Amine MB |
| Coco amine | Nihon Yushi | Amine FB |

Other reagents such as 2-ethylhexyl amine; dibutyl amine, ethylene diamine, monoethanolamine and n-butyl amine were all made by Tokyo Kasei.

EXPERIMENTAL PROCEDURE

The test oil (100 ml) was poured into a 200 ml glass container; the specified quantity of viscosity inhibitor was added to the container and heated to 180° C. for 15 hours. When the test oil was cooled to 25° C., its viscosity was measured with a BL type revolving viscometer (made by Tokyo Keiki). The test oil was quench oil obtained from an ethylene plant (containing less than 0.1 wt. % styrene; less than 0.1 wt. % methylstyrene; less than 0.1 wt. % divinylbenzene and less than 0.1 wt. % indene). The tower bottom oil and oil quench tower reflux oil (containing 30 wt. % styrene; 14.5 wt. % methylstyrene; 0.2 wt. % divinylbenzene and 9.0 wt. % indene) were mixed at the mixing ratio of 9:1 (in volume). The results of these tests are shown in Tables IV and V.

TABLE IV

Inventive Examples

| | Viscosity inhibitor composition | | | | Tested oil | |
|---|---|---|---|---|---|---|
| Ex. | Sulfonic acid or salt | (dosage: ppm) | Polymerization inhibitor | (dosage: ppm) | Tower bottom oil, Viscosity (cp, 25° C.) | Mixture of tower bottom oil and reflux oil; Viscosity (cp, 25° C.) |
| 1 | A | (1000) | — | | 12,300 | 1,950 |
| 2 | B | (100) | — | | 14,000 | 2,600 |
| 3 | B | (500) | — | | 9,500 | 1,950 |
| 4 | B | (1000) | — | | 8,800 | 1,350 |
| 5 | B | (10,000) | — | | 5,200 | 750 |
| 6 | C | (500) | — | | 10,500 | 1,800 |
| 7 | C | (1000) | — | | 9,000 | 1,450 |
| 8 | D | (1000) | — | | 9,200 | 1,550 |
| 9 | E | (1000) | — | | 10,400 | 1,800 |
| 10 | F | (1000) | — | | 11,500 | 1,850 |
| 11 | G | (1000) | — | | 9,800 | 1,750 |
| 12 | H | (1000) | — | | 9,000 | 1,500 |
| 13 | I | (1000) | — | | 9,600 | 1,750 |
| 14 | J | (1000) | — | | 13,700 | 2,050 |
| 15 | K | (1000) | — | | 11,200 | 1,900 |
| 16 | A | (300) | — | | 9,200 | 1,800 |
| | B | (500) | | | | |
| 17 | A | (500) | — | | 9,900 | 1,640 |
| | C | (500) | | | | |
| 18 | B | (800) | TBC | (200) | 9,200 | 850 |
| 19 | B | (800) | BHT | (200) | 9,100 | 1,000 |
| 20 | B | (800) | BPA | (200) | 8,800 | 850 |
| 21 | B | (800) | DEHA | (200) | 9,000 | 700 |
| 22 | B | (800) | DPA | (200) | 9,000 | 900 |
| 23 | B | (800) | TBC | (100) | 8,700 | 850 |
| | B | (800) | BPA | (100) | | |

TABLE V

Comparative Examples

| | Viscosity inhibitor composition | | | | Tested oil | |
|---|---|---|---|---|---|---|
| Ex. | Sulfonic acid or salt | (dosage: ppm) | Polymerization inhibitor | (dosage: ppm) | Tower bottom oil, Viscosity (cp, 25° C.) | Mixture of tower bottom oil and reflux oil; Viscosity (cp, 25° C.) |
| 24 | None | | — | | 17,900 | 3,150 |
| 25 | L | (1000) | — | | 17,300 | 3,000 |
| 26 | L | (800) | TBC | (200) | 17,500 | 2,850 |
| 27 | L | (800) | DPA | (200) | 17,200 | 2,900 |
| 28 | — | | TBC | (200) | 17,800 | 2,700 |
| 29 | — | | DEHA | (1000) | 17,300 | 1,550 |
| 30 | — | | DPA | (1000) | 17,600 | 2,850 |
| 31 | — | | TBC | (500) | 17,000 | 2,600 |
| | | | BPA | (500) | | |
| 32 | — | | Polymethacrylate family dispersant | (1000) | 18,400 | 3,300 |

As a result of the above experiments, it was confirmed that the increase viscosity of hydrocarbon in the bottom section of oil quench tower was effectively inhibited by adding the combination of sulfonic acid or its salt and polymerization inhibitor, as described in this invention, to the test oil. Note that Example 24 serves as the control against which inventive Examples 1–23 may be compared. The results of Examples 1–23 show considerably greater reduction in viscosity than do the results of Examples 25–32.

With the hydrocarbon viscosity inhibitor or reducer composition of this invention and the method employing it, the viscosity of hydrocarbon treated, such as in the bottom section of an oil quench tower, e.g., can be reduced and its increase inhibited. Further, gasoline yield is increased, the load on the bottom mp is reduced, pipings are prevented from clogging, refluxing rate in the oil ench tower is reduced, the temperature of the tower bottom section is increased to reduce the amount of heating steam used for the succeeding processes, etc., thus improving the economic effect of the entire process.

In the foregoing specification, the invention has been described with reference to specific embodiments thereof. However, it will be evident that various modifications and changes can be made thereto without departing from the broader spirit or scope of the invention as set forth in the appended claims. Accordingly, the specification is to be regarded in an illustrative rather than a restrictive sense. For example, specific viscosity inhibitors falling within the claimed parameters, but not specifically identified or tried are anticipated to be within the scope of this invention. Further, specific combinations of viscosity inhibitors and polymerization inhibitors within the claimed scope but not specifically identified or experimented with are anticipated to be within the scope of this invention.

We claim:

1. A method of inhibiting the viscosity of a hydrocarbon comprising adding a hydrocarbon viscosity inhibitor composition to the hydrocarbon in the absence of adding of dialkylhydroxylamine, where the hydrocarbon viscosity inhibitor composition comprises a sulfonic acid or salt thereof of the formula:

$$R'-SO_3(X)_n$$

where R' is selected from the group consisting of a straight or branched alkyl group of 4–32 carbon atoms;

an alkyl-substituted benzene nucleus, where the alkyl group is a straight or branched alkyl group of 4–32 carbon atoms; and an alkyl-substituted naphthalene nucleus, where the alkyl group is a straight or branched alkyl group of 4–32 carbon atoms;

X is selected from the group consisting of hydrogen, alkali metal, and alkali earth metal, primary amine salt, secondary amine salt, tertiary amine salt; where any of the amine salts may be substituted with a straight or branched alkyl group of 1–22 carbon atoms, and further where the straight or branched alkyl group of 1–22 carbon atoms may contain a hydroxy or an alkoxy group; and n is selected from the group consisting of 1 or ½; and a polymerization inhibitor selected from the group consisting of an aromatic amine, and a phenol.

2. The method of claim 1 where in the adding of the hydrocarbon viscosity inhibitor composition to the hydrocarbon, the weight ratio of polymerization inhibitor to sulfonic acid or salt in the viscosity inhibitor composition is 10:1 or less.

3. The method of claim 1 where in the adding of the hydrocarbon viscosity inhibitor composition to the hydrocarbon, the amount of hydrocarbon viscosity inhibitor composition added ranges from about 10 ppm to 10,000 ppm based on hydrocarbon.

4. The method of claim 1 where the adding of the hydrocarbon viscosity inhibitor composition comprises adding the hydrocarbon viscosity inhibitor composition to a hydrocarbon in a bottom section of an oil quench tower.

5. A method of inhibiting the viscosity of a hydrocarbon comprising adding a hydrocarbon viscosity inhibitor composition to the hydrocarbon in the absence of adding of dialkylhydroxylamine where the amount of hydrocarbon viscosity inhibitor composition ranges from about 10 ppm to 10,000 ppm based on the hydrocarbon, and where viscosity inhibitor composition comprises a sulfonic acid or salt thereof of the formula:

$$R'-SO_3(X)_n$$

where R' is selected from the group consisting of a straight or branched alkyl group of 4–32 carbon atoms;

an alkyl-substituted benzene nucleus, where the alkyl group is a straight or branched alkyl group of 4–32 carbon atoms; and an alkyl-substituted naphthalene nucleus, where the alkyl group is a straight or branched alkyl group of 4–32 carbon atoms;

X is selected from the group consisting of hydrogen, alkali metal, and alkali earth metal, primary amine salt, secondary amine salt, tertiary amine salt; where any of the amine salts may be substituted with a straight or branched alkyl group of 1–22 carbon atoms, and further where the straight or branched alkyl group of 1–22 carbon atoms may contain a hydroxy or an alkoxy group; and n is selected from the group consisting of 1 or ½; and a polymerization inhibitor selected from the group consisting of an aromatic amine, and a phenol;

where the weight ratio of polymerization inhibitor to sulfonic acid or salt thereof is 10:1 or less.

6. The method of claim 5 where the adding of the hydrocarbon viscosity inhibitor composition comprises adding the hydrocarbon viscosity inhibitor composition to a hydrocarbon in a bottom section of an oil quench tower.

* * * * *